(12) United States Patent
Sambelashvili et al.

(10) Patent No.: US 11,191,969 B2
(45) Date of Patent: Dec. 7, 2021

(54) ADAPTIVE CARDIAC RESYNCHRONIZATION THERAPY USING A SINGLE MULTI-ELECTRODE CORONARY SINUS LEAD

(71) Applicant: Medtronic, Inc., Minneapolis, MN (US)

(72) Inventors: Aleksandre Sambelashvili, Maple Grove, MN (US); Yong Cho, Excelsior, MN (US); Jeffrey Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 438 days.

(21) Appl. No.: 15/967,015

(22) Filed: Apr. 30, 2018

(65) Prior Publication Data

US 2019/0329034 A1  Oct. 31, 2019

(51) Int. Cl.
*A61N 1/368* (2006.01)
*A61B 5/00* (2006.01)
(Continued)

(52) U.S. Cl.
CPC .............. *A61N 1/368* (2013.01); *A61B 5/287* (2021.01); *A61B 5/341* (2021.01); *A61B 5/366* (2021.01);
(Continued)

(58) Field of Classification Search
CPC .............. A61N 1/3684; A61N 1/36843; A61N 1/36842; A61N 1/3682; A61N 1/39622;
(Continued)

(56) References Cited

U.S. PATENT DOCUMENTS

| 5,117,824 A | 6/1992 | Keimel et al. |
| 6,393,316 B1 | 5/2002 | Gillberg et al. |
| (Continued) | | |

FOREIGN PATENT DOCUMENTS

| WO | 2009114360 A1 | 9/2009 |
| WO | 2017011659 A1 | 1/2017 |

OTHER PUBLICATIONS

(PCT/US2019/029652) PCT Notification of Transmittal of the International Search Report and the Written Opinion of the International Searching Authority, dated Nov. 13, 2019, 10 pages.
(Continued)

*Primary Examiner* — Deborah L Malamud
(74) *Attorney, Agent, or Firm* — Mueting Raasch Group (57) ABSTRACT

A method and implantable medical device system for delivering a cardiac pacing therapy that includes suspending delivery of the LV cardiac pacing therapy and sensing far-field cardiac signals via one or more far-field sensing vectors formed between a plurality of electrodes positioned on a single-pass coronary sinus lead. Far-field signal features are determined in response to the sensed far-field cardiac signals, a first offset interval and a second offset interval are determined in response to the determined far-field signal features, and an AV delay of the LV cardiac pacing therapy is adjusted in response to the determined first offset interval and second offset interval. Delivery of the LV cardiac pacing therapy having the adjusted AV delay is subsequently resumed.

20 Claims, 9 Drawing Sheets

(51) Int. Cl.
*A61N 1/372* (2006.01)
*A61B 5/287* (2021.01)
*A61B 5/341* (2021.01)
*A61B 5/366* (2021.01)
*A61N 1/375* (2006.01)
*A61N 1/05* (2006.01)

(52) U.S. Cl.
CPC .......... *A61B 5/686* (2013.01); *A61N 1/37211* (2013.01); *A61B 2562/0209* (2013.01); *A61N 1/37512* (2017.08); *A61N 2001/0585* (2013.01)

(58) Field of Classification Search
CPC .... A61N 1/368; A61N 1/365; A61N 1/36139; A61N 1/3702; A61N 1/622; A61N 1/362; A61N 1/37; A61N 1/37512; A61N 1/37516; A61N 2001/0585; A61B 5/0452; A61B 5/04085; A61B 5/0456; A61B 5/04012; A61B 5/04011; A61B 5/0422; A61B 5/6869; A61B 5/0468; A61B 5/4836; A61B 5/7282; A61B 5/04; A61B 5/0402; A61B 5/02
See application file for complete search history.

(56) References Cited

U.S. PATENT DOCUMENTS

| | | | |
|---|---|---|---|
| 6,738,669 B1 | 5/2004 | Sloman et al. | |
| 6,907,286 B1* | 6/2005 | Kroll | A61N 1/3622 607/14 |
| 7,062,315 B2 | 6/2006 | Koyrakh et al. | |
| 7,440,803 B2 | 10/2008 | Ni et al. | |
| 8,909,329 B2 | 12/2014 | Prakash et al. | |
| 9,014,330 B2 | 4/2015 | Takayama | |
| 9,089,276 B2 | 7/2015 | Xi et al. | |
| 9,095,720 B2 | 8/2015 | Keel et al. | |
| 2009/0149907 A1* | 6/2009 | Perschbacher | A61N 1/3987 607/17 |
| 2013/0053918 A1 | 2/2013 | Sambelashvili et al. | |
| 2013/0197599 A1 | 8/2013 | Sambelashvili et al. | |
| 2014/0046389 A1 | 2/2014 | Anderson et al. | |

OTHER PUBLICATIONS

Office Action from U.S. Appl. No. 15/966,960 dated Mar. 3, 2020, 9 pages.
Office Action from U.S. Appl. No. 15/966,960 dated Sep. 29, 2020, 10 pages.
Office Action from U.S. Appl. No. 15/966,960 dated Mar. 22, 2021, 9 pages.

* cited by examiner

ADAPTIVE CARDIAC RESYNCHRONIZATION THERAPY USING A SINGLE MULTI-ELECTRODE CORONARY SINUS LEAD

FIELD

The present disclosure pertains to cardiac pacing methods and systems, and, more particularly, to a method and apparatus for delivering cardiac pacing therapy in an implantable medical device system having only a single multi-electrode coronary sinus lead.

BACKGROUND

The activity of a normal, healthy heart involves the synchronized contraction of the atria and ventricles of the heart. Blood is received into the atria, which contract, forcing the blood into the ventricles. Subsequent contraction of the ventricles then causes the blood to be pumped through the body and eventually returned to the atria. The contractions of the chambers of the heart are caused by coordinated electrical activation of portions of the cardiac muscle.

The heartbeat cycle begins with the generation of an electrical impulse by a bundle of fibers located in the sinoatrial node of the heart, near the upper portion of the right atrium at the entrance to the superior vena cava. This impulse propogates across the atria, stimulating the atrial muscles and causing the atrial contraction, which forces blood into the ventricles. An atrial contraction is manifested as the so-called "P-wave" in an electrocardiographic signal. The electrical impulse conducted through the atrial muscle is then received at the partition wall immediately beside the valve between the right atrium and right ventricle, at the atrio-ventricular or A-V node. The A-V node introduces a slight delay in the transmission of the electrical impulse to the ventricles. This A-V delay is typically on the order of 100 milliseconds. After the A-V delay, the electrical impulse is conducted to the ventricles, causing the ventricular contraction which is manifested as the "QRS complex" of an electrocardiographic signal. Subsequent repolarization and relaxation of the ventricular muscles occurs at the end of the cardiac cycle, which is manifested as the "T-wave" portion of an electrocardiographic signal.

For patients in which the above-described conduction of electrical impulses through the cardiac muscle is somehow impaired, a pacemaker can provide an artificial electrical stimulus where no natural electrical impulse is present. Thus, for example, a ventricular pacemaker can function to cause ventricular contractions in patients in which the natural electrical cardiac impulse is, for some reason, not transmitted across the A-V node. It is important, however, that any artificial stimulating pulses be delivered at appropriated times, so that proper synchronization of atrial and ventricular action is maintained. In addition, it is known that electrical impulses being delivered to the cardiac muscle during the repolarization phase at the end of the cardiac cycle can cause the onset of tachyarrhythmias. It is therefore important that the pacemaker be prevented from delivering stimulating pulses during the T-wave.

In order to maintain A-V synchrony, and to prevent delivery of pacing pulses at undesirable times, pacemakers are preferably capable of detecting either atrial activity, ventricular activity, or both, as manifested by the P-wave and QRS complex (or more typically the R-wave), respectively, via atrial and ventricular cardiac electrogram signals sensed by the pacemaker.

Pacemakers are generally characterized by which chambers of the heart they are capable of sensing, the chambers to which they deliver pacing stimuli, and their responses, if any, to sensed intrinsic electrical cardiac activity. Some pacemakers deliver pacing stimuli at fixed, regular intervals without regard to naturally occurring cardiac activity. More commonly, however, pacemakers sense electrical cardiac activity in one or both of the chambers of the heart and inhibit or trigger delivery of pacing stimuli to the heart based on the occurrence and recognition of sensed intrinsic electrical events.

Cardiac resynchronization therapy (CRT) may correct the symptoms of electrical dyssynchrony by providing pacing therapy through medical electrical leads to one or both ventricles or atria to encourage earlier activation of the left or right ventricles. By pacing the contraction of the ventricles, the ventricles may be controlled so that the ventricles contract in synchrony. One form of CRT is fusion pacing, which typically involves left ventricle (LV) only pacing with an electrode on the LV medical electrical lead in coordination with the intrinsic right ventricle (RV) activation. Effective fusion requires, for example, that the timing of the LV pacing be in synchrony with the earliest activation on the RV chamber. For example, in a fusion pacing configuration, a medical device delivers one or more fusion pacing pulses to a later-contracting left ventricle (LV) in order to pre-excite the LV and synchronize the depolarization of the LV with the depolarization of the earlier contracting right ventricle (RV). The ventricular activation of the LV may "fuse" (or "merge") with the ventricular activation of the RV that is attributable to intrinsic conduction of the heart. In this way, the intrinsic and pacing-induced excitation wave fronts may fuse together such that the depolarization of the LV is resynchronized with the depolarization of the RV.

In order to ensure that the timing of delivery of the LV pacing is in synchrony with the earliest activation on the RV chamber, sensing of activation of the RV chamber is of critical importance. Current therapy systems for delivering CRT typically include a right atrial lead extending into the right atrium (RA) of the patient's heart, a right ventricle lead that extends through the right atrium and into the right ventricle (RV), and a left ventricle lead that extends through the right, and into the coronary sinus to a region adjacent to the free wall of the left ventricle (LV) of the heart. Therefore, sensing of activation of the RV for enabling effective timing of delivery of LV paving to be determined can be done directly via the RV lead.

SUMMARY

The present disclosure is directed to a method and implantable medical device system for delivering LV pacing therapy that includes only a single pass coronary sinus lead. The single pass coronary sinus lead includes electrodes, which are spaced in a manner so that when the lead is positioned within the coronary sinus of the patient, the electrodes may be located near the left ventricle, and near the left atrium and/or the right atrium. In some examples, an electrode near the left ventricle may be located near the intra-ventricular septum.

In this way, the lead according to the present disclosure is designed to provide pacing and sensing of both the atria and the ventricles without requiring the introduction of a lead or an electrode into the right ventricle and may be referred to as a single-pass, left-sided, DDD lead. The lead may be referred to as single-pass in that the single lead places electrodes proximate to both an atrium and a ventricle, and as left-sided in that the lead places electrodes proximate to the left ventricle, e.g., via the coronary sinus, rather than the right ventricle. The lead may also be referred to as single-pass coronary sinus lead.

According to one example of the present disclosure, a method for delivering a left ventricular (LV) cardiac pacing therapy to a patient, comprising: suspending delivery of the LV cardiac pacing therapy; sensing far-field cardiac signals via one or more far-field sensing vectors formed between a plurality of electrodes; determining far-field signal features in response to the sensed far-field cardiac signals; determining a first offset interval and a second offset interval in response to the determined far-field signal features; adjusting an AV delay of the LV cardiac pacing therapy in response to the determined first offset interval and second offset interval; and resuming delivery of the LV cardiac pacing therapy having the adjusted AV delay.

According to another example of the present disclosure, an implantable medical device system for delivering a cardiac pacing therapy to a patient, comprises: an implantable medical device housing; a single-pass coronary sinus lead capable of being electrically coupled to the housing; a plurality of electrodes positioned along the single-pass coronary sinus lead to sense a far-field cardiac signal of the patient and to deliver cardiac pacing therapy; and a processor positioned within the housing and configured to suspend delivery of the LV cardiac pacing therapy, sense far-field cardiac signals via one or more far-field sensing vectors formed between a plurality of electrodes, determine far-field signal features in response to the sensed far-field cardiac signals, determine a first offset interval and a second offset interval in response to the determined far-field signal features, adjust an AV delay of the LV cardiac pacing therapy in response to the determined first offset interval and second offset interval, and resume resuming delivery of the LV cardiac pacing therapy having the adjusted AV delay.

Another example of the present disclosure includes a non-transitory computer readable medium storing instructions which causes an implantable medical device to perform a method the method comprising: suspending delivery of a left ventricular (LV) cardiac pacing therapy; sensing far-field cardiac signals via one or more far-field sensing vectors formed between a plurality of electrodes positioned on a single-pass coronary sinus lead; determining far-field signal features in response to the sensed far-field cardiac signals; determining a first offset interval and a second offset interval in response to the determined far-field signal features; adjusting an AV delay of the LV cardiac pacing therapy in response to the determined first offset interval and second offset interval; and resuming delivery of the LV cardiac pacing therapy having the adjusted AV delay.

DETAILED DESCRIPTION OF EXEMPLARY EMBODIMENTS

It will be apparent to a skilled artisan that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale.

In general, the present disclosure is directed to a method of sensing activation of the right ventricle for determining timing of delivery of a cardiac resynchronization pacing therapy in an implantable medical device system that does not include a right ventricular lead positioned directly within the RV chamber. For example, the medical device system may include a housing or can and a single lead that is capable of providing left ventricular LV DDD pacing electrically coupled to the housing. The lead of the present disclosure includes four electrodes, which are spaced in a manner so that when the lead is positioned within the coronary sinus of the patient, the electrodes may be located near the left ventricle, and near the left atrium and/or the right atrium. In some examples, an electrode near the left ventricle may be located near the intra-ventricular septum.

In this way, the lead according to the present disclosure is designed to provide pacing and sensing of both the atria and the ventricles without requiring the introduction of a lead or an electrode into the right ventricle and may be referred to as a single-pass, left-sided, DDD lead. The lead may be referred to as single-pass in that the single lead places electrodes proximate to both an atrium and a ventricle, and as left-sided in that the lead places electrodes proximate to the left ventricle, e.g., via the coronary sinus, rather than the right ventricle. The lead may also be referred to as single-pass coronary sinus lead.

Figure 1:
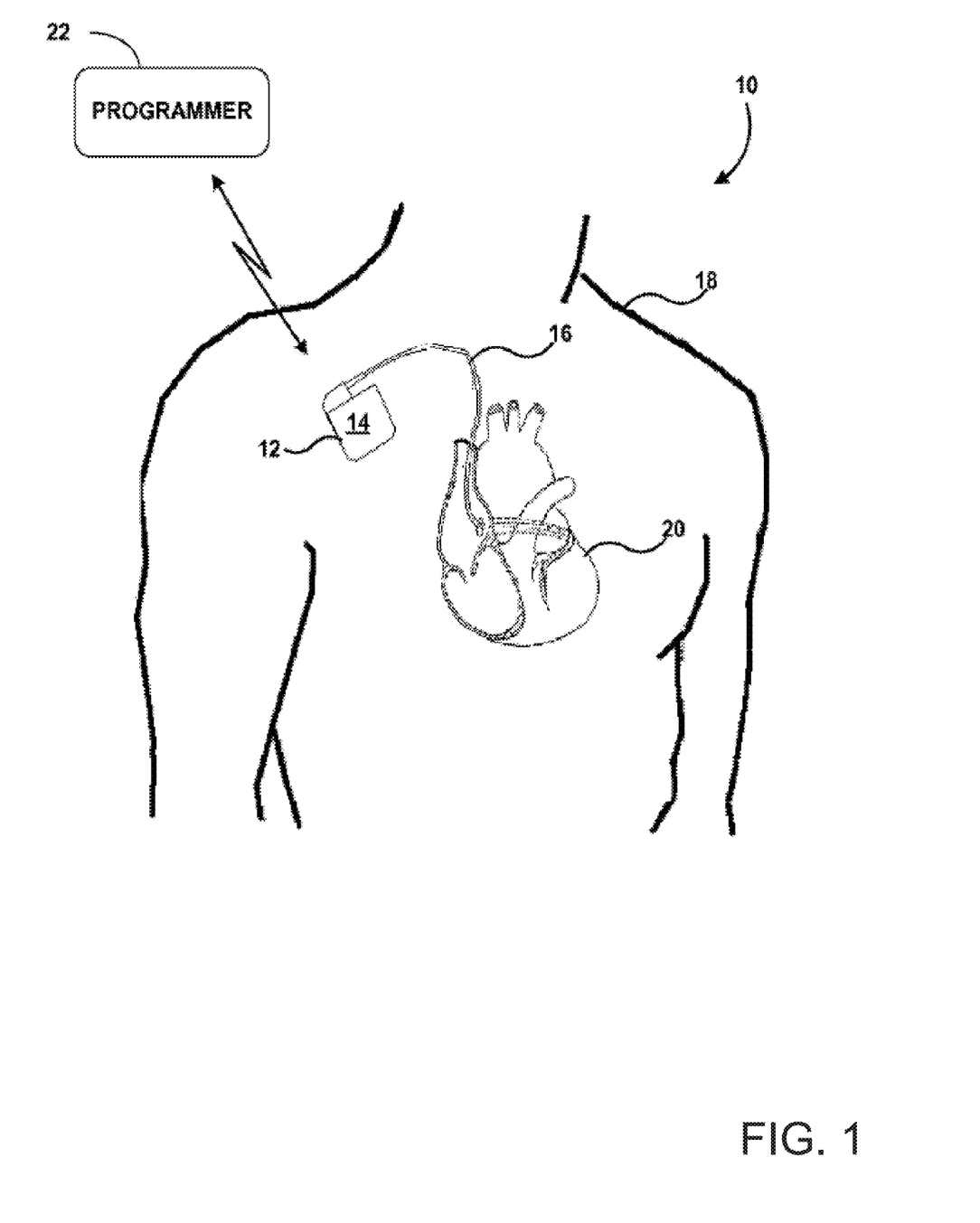
FIG. 1 is a conceptual diagram illustrating an example medical device system for delivering pacing stimuli to a patient's heart in accordance with the present disclosure.

FIG. 1 is a conceptual diagram illustrating an example medical device system for delivering pacing stimuli to a patient's heart in accordance with the present disclosure. As illustrated in FIG. 1, in one example, an implantable medical device system 10 may include an implantable medical device (IMD) 12 and an implantable medical lead 16 electrically coupled to the IMD 12. In the example shown in FIG. 1, system 10 is implanted within a patient 18 to deliver electrical stimulation therapy to the heart 20 of patient 18. Patient 18 ordinarily, but not necessarily, will be a human patient.

In the example shown in FIG. 1, IMD 12 is a cardiac pacemaker, cardioverter, defibrillator, or pacemaker-cardioverter-defibrillator (PCD) that generates therapeutic electrical stimulation for pacing, cardioversion or defibrillation, which may take the form of pulses, e.g., about 1 to about 5 volt pacing pulses at a rate of about 50 to about 150 pulses per minute, or infrequent cardioversion/defibrillation stimuli of about 100 to about 800 volts. Lead 16 includes four electrodes that are each positioned within (e.g., intravascularly) heart 20 in order to deliver the therapeutic electrical stimulation from IMD 12 to the heart 20.

In the illustrated example, a distal end of lead 16 is positioned proximate to the left ventricle (LV) of patient 18, and more particularly, within the coronary sinus or a coronary vein accessed via the coronary sinus. In the illustrated example, lead 16 is configured for intravenous introduction into the heart 20. For example, lead 16 may have a lead body diameter between about 1 and about 3 millimeter. When lead 16 is positioned within the coronary sinus or coronary vein, the four electrodes (not shown in FIG. 1) may be positioned so that the two most proximal electrodes are positioned within or near the right atrium (RA) in close proximity to the AV node. In some examples, one electrode may be in the RA and one electrode may be within the coronary sinus. The third electrode may be located in the great cardiac vein and the fourth, and most distal, electrode may be located in one of the tributaries of the great coronary vein. For example, the fourth electrode may be located in the lateral coronary vein, the anterior coronary vein, or the anterior-lateral coronary vein. As described in further detail below, this configuration of electrodes allows for atrial sensing and pacing as well as ventricular sensing and pacing, as needed, using a single lead. Housing 14 of IMD 12 may be used as an anode in some examples.

To facilitate passage down narrow vessels, the electrodes of lead 16 are nearly the same diameter as the lead body, usually a fraction of a millimeter thicker to make sure they contact the vessel wall. Likewise, the helix fixation member 32 (FIG. 2) may also be slightly thicker than, e.g., a fraction of a millimeter thicker than, the lead body. Electrodes are typically about 0.2 to about 0.5 cm long. The whole lead is about 50 to about 100 cm in length, depending on the size of the patient.

As illustrated in FIG. 1, system 10 may also include a programmer 22, which may be a handheld device, portable computer, or workstation that provides a user interface to a clinician or other user. The clinician may interact with the user interface to program stimulation and sensing parameters for IMD 12, which may include, as examples, the electrodes of lead 16 which are activated for providing stimulation versus sensing, as well as selection from among different pacing modes, rate-response modes, inter-chamber intervals, arrhythmia detection algorithms, arrhythmia termination therapy progressions.

Programmer 22 supports telemetry (e.g., radio frequency telemetry) with IMD 12 to download stimulation parameters and, optionally, upload operational or physiological data stored by IMD 12. In this manner, the clinician may periodically interrogate IMD 12 to evaluate efficacy and, if necessary modify the operational parameters of the IMD. IMD 12 and programmer 22 may communicate via wireless communication as shown in FIG. 1. Programmer 22 may, for example, communicate via wireless communication with IMD 12 using RF telemetry techniques known in the art.

In some examples, at least one of the electrodes of lead 16 may function as a sensor that senses a physiological parameter of patient 12, such as, but not limited to, electrogram (EGM) parameters, a heart rate, QRS width, or atrioventricular (AV) dissociation. Sense electrodes may be the same electrodes used for delivery of electrical stimulation to patient 18, or different electrodes.

Figure 2:
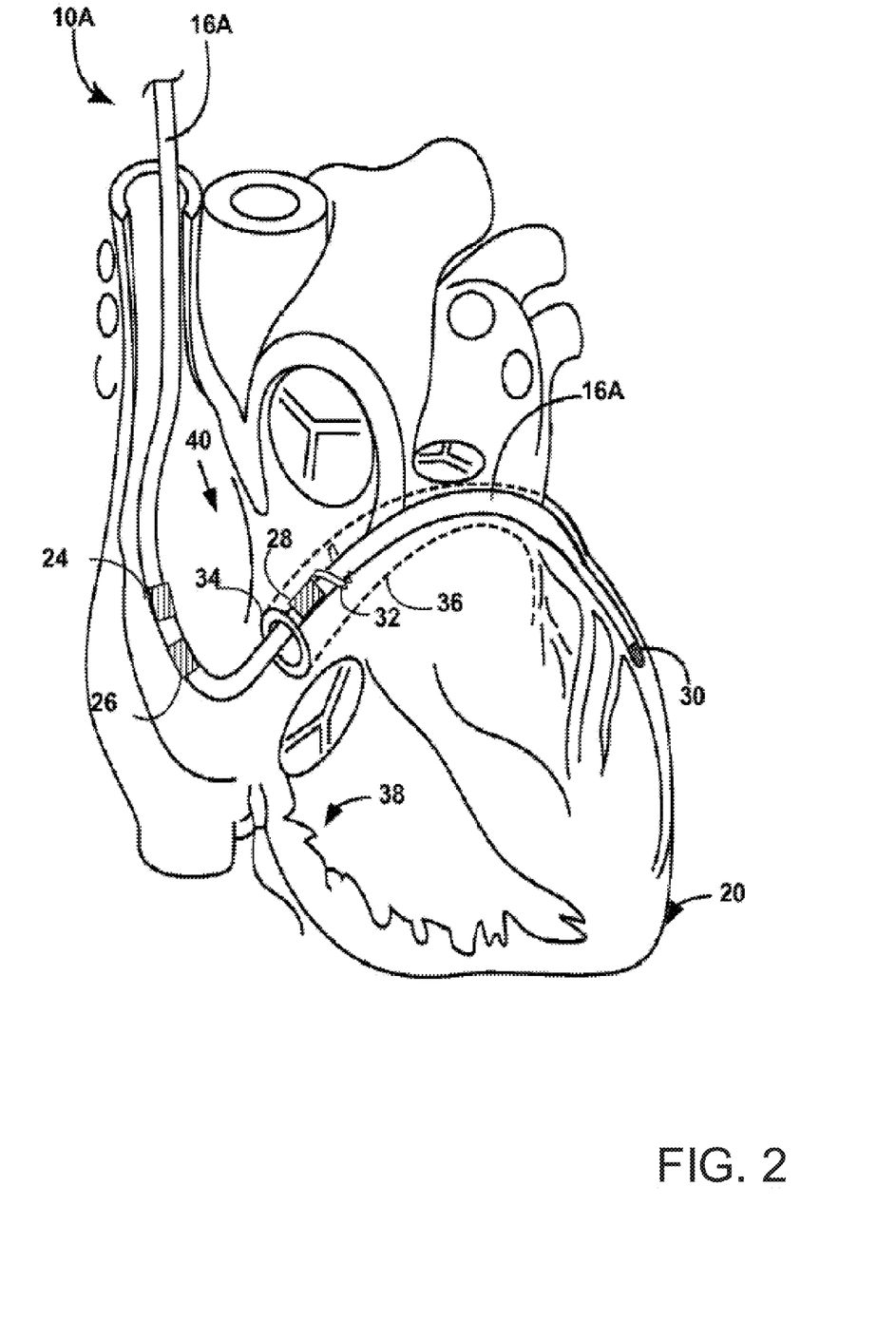
FIG. 2 is a conceptual diagram illustrating an example configuration of a lead of a medical device system for delivering a pacing therapy to a patient's heart, in accordance with the present disclosure.

FIG. 2 is a conceptual diagram illustrating an example configuration of a lead of a medical device system for delivering a pacing therapy to a patient's heart, in accordance with the present disclosure. As illustrated in FIG. 2, a lead 16A of a medical device system 10A may include electrodes 24, 26, 28 and 30, along with a helix fixation member 32. In some examples, helix fixation member 32 may also be an electrode 28, e.g., helix fixation member 32 is conductive and acts as, or as part of, electrode 28. Lead 16A may be anchored to the wall of the coronary sinus 36, near the ostium 34 via helix fixation member 32. Lead 16A may be anchored by turning the lead clockwise to embed the helix fixation member 32 into the wall of the coronary sinus 36 when the electrodes are situated as desired within the heart 20.

As illustrated in FIG. 2, the electrodes of lead 16 are spaced so that electrodes 24 and 26 are located in RA 40. In some examples, electrodes 24 and 26 are floating electrodes within RA 40, e.g., do not necessarily contact the tissue of RA 40. For example, electrodes 24 and 26 may be floating atrial sense electrodes that function in a manner similar to floating sense electrodes in a conventional VDD lead. In some examples, electrodes 24 and 26 are located near the heart septum. In the example of FIG. 2, electrode 28 is located within coronary sinus 36, and electrode 30 is located at the distal end of lead 16, within one of the tributary veins of the great coronary vein. For example, electrode 30 may be located in the lateral coronary vein, the anterior coronary vein, or the anterior-lateral coronary vein. The tributary vein is selected so that electrode 30 is roughly adjacent the left ventricle (LV) and not as near the right ventricle (RV) apex. Electrodes 24 and 26 may be located less than approximately 1 cm apart. In some examples, electrodes 24 and 26 may be less than approximately 0.5 cm apart. The close spacing of atrial electrodes 24 and 26 may help to avoid R-wave over sensing, including far-field R-wave oversensing. In addition, the location of electrodes may aide in detecting the occurrence of an A-V block. In some examples, either of electrodes 24 and 26 may used in a unipolar configuration with an electrode formed on or by housing 14 to sense atrial activity. In some examples, electrode 28 may serve as an atrial pace cathode, with the housing 14 of IMD 12 functioning as the atrial pace anode. Electrode 28 may also serve as the ventricular sense-anode while electrode 30 may serves as the ventricular sense-cathode. The housing 14 may also function as an anode when electrode 30 delivers stimulation to LV 40.

Figure 3:
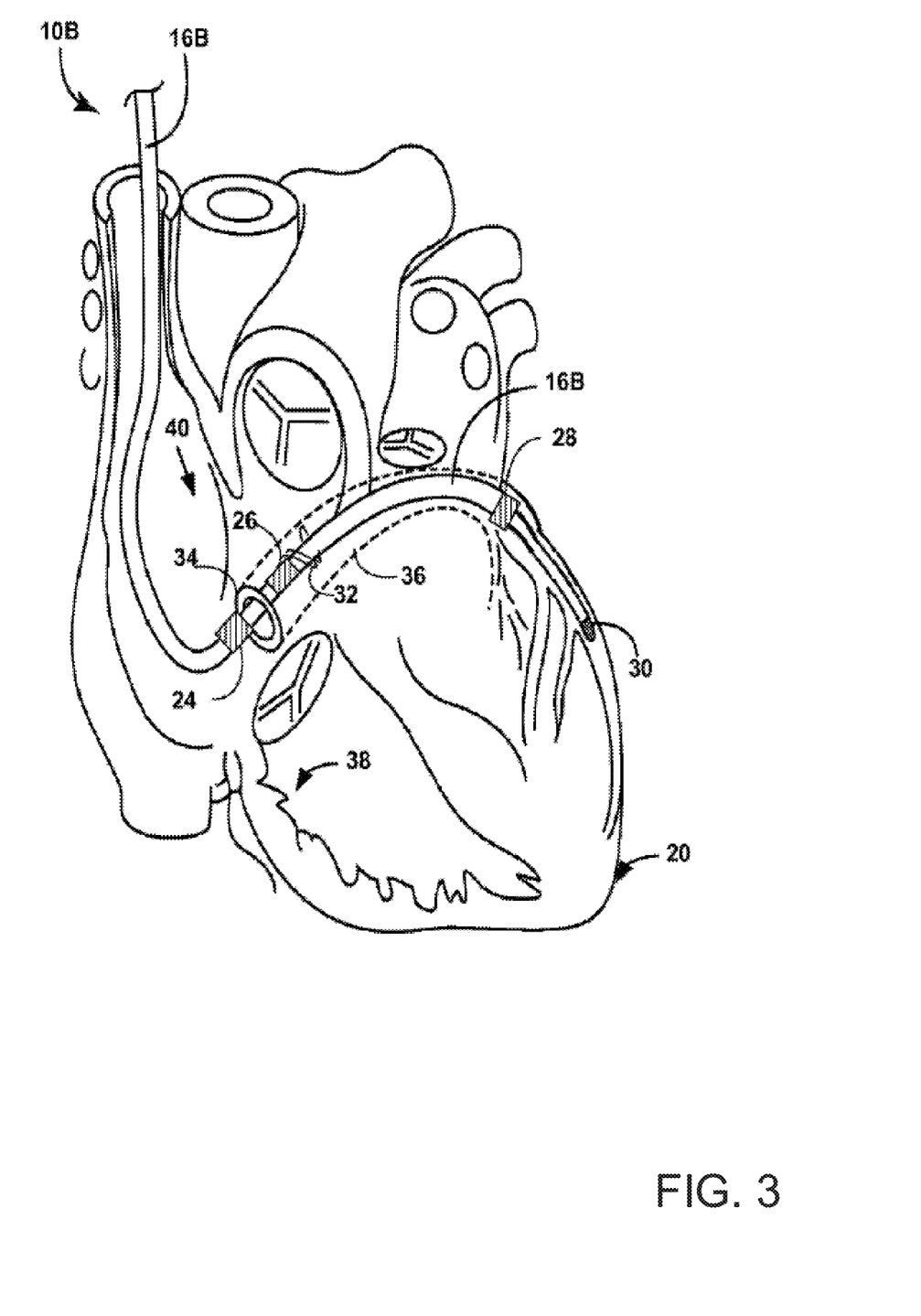
FIG. 3 is a conceptual diagram illustrating an example configuration of a lead of a medical device system for delivering a pacing therapy to a patient's heart, in accordance with the present disclosure.

FIG. 3 is a conceptual diagram illustrating an example configuration of a lead of a medical device system for delivering a pacing therapy to a patient's heart, in accordance with the present disclosure. As illustrated in FIG. 3, a lead 16B of an implantable medical device system 10B may include electrodes 24, 26, 28 and 30, along with a helix fixation member 32, which may act as or be electrically coupled to electrode 26. Lead 16B may be anchored to the wall of the coronary sinus 36, near ostium 34 via helix fixation member 32. Lead 16B may be anchored by turning the lead clockwise to embed the helix fixation member 32 into the wall of the coronary sinus 36 when the electrodes are situated as desired within the heart. As illustrated in FIG.

3, the electrodes of lead 16 are spaced so that electrode 24 is located within RA 40, electrode 26 is located proximate to coronary sinus ostium 34, electrode 28 is located in the great cardiac vein, near the left atrium, and electrode 30 is located at the distal end of lead 16, within one of the tributary veins of the great coronary vein. For example, electrode 30 may be located in the lateral coronary vein, the anterior coronary vein, or the anterior-lateral coronary vein. The tributary vein is selected so that electrode 30 is roughly adjacent the left ventricle (LV) and not as near the right ventricle (RV) apex.

Electrodes 24 and 26 may act as a bipolar pair to sense atrial activity. Electrodes 24 and 26 may be located less than approximately 1 cm apart. In some examples, electrodes 24 and 26 may be less than approximately 0.5 cm apart. The close spacing of atrial electrodes 24 and 26 may help to avoid R-wave over sensing, including far-field R-wave oversensing. In addition, the location of electrodes may aide in detecting the occurrence of an A-V block. In some examples, either of electrodes 24 and 26 may be used in a unipolar configuration with an electrode formed on or by housing 14 to sense atrial activity.

In some examples, electrode 26 may serve as an atrial pace cathode, with the housing 14 of IMD 12 functioning as the atrial pace anode. Electrode 28 may serve as the ventricular sense-anode while electrode 30 may serves as the ventricular sense-cathode, or either of electrodes 28 and 30 may be used in a unipolar configuration to sense electrical activity of the ventricles. Furthermore, electrodes 28 and 30 may be used to deliver bipolar pacing or other stimulation to LV 40, or either or both of electrodes 28 and 30 may be used in a unipolar configuration with an electrode of housing 14 to deliver unipolar stimulation. The housing 14 may function as an anode when electrodes 28 or 30 stimulate. In some examples, both of electrodes 28 and 30 may be used in a unipolar configuration to deliver sequential pacing to the ventricles. For example, electrode 28 may provide a first pacing pulse. A delay of approximately 10 milliseconds may be programmed between the pacing pulse from electrode 28 and a second pacing pulse from electrode 30. During delay electrode 30 is in sensing mode. If electrode 30 senses that the pulse from electrode 28 was successful in capturing the heart, then the pacing pulse from electrode 30 is inhibited. However, if the pacing pulse from electrode 28 does not result in capture, then electrode 30 provides the second pacing pulse.

Figure 4:
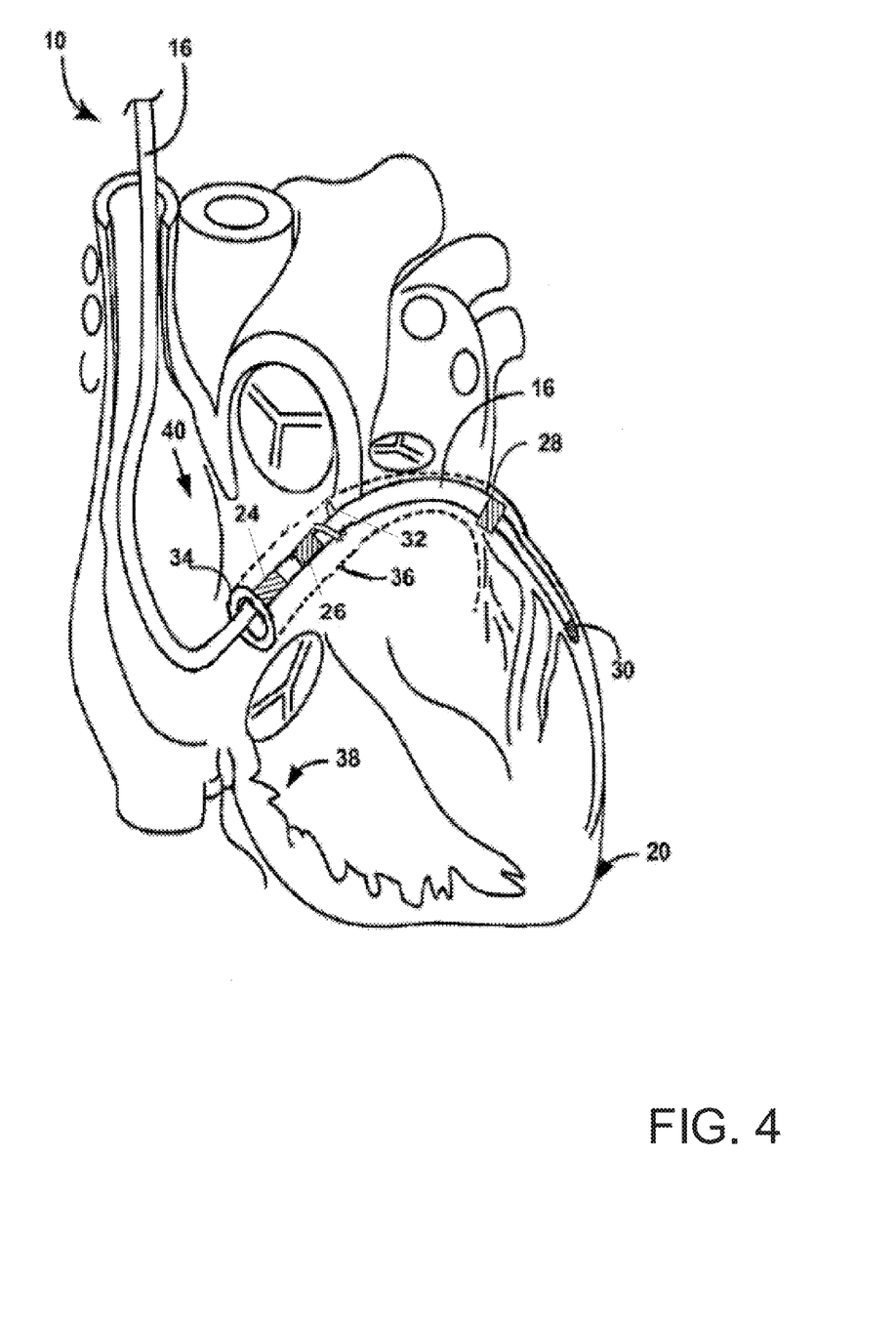
FIG. 4 is a conceptual diagram illustrating an example configuration of a lead of a medical device system for delivering a pacing therapy to a patient's heart, in accordance with the present disclosure.

FIG. 4 is a conceptual diagram illustrating an example configuration of a lead of a medical device system for delivering a pacing therapy to a patient's heart, in accordance with the present disclosure. As illustrated in FIG. 4, a lead 16C of an implantable medical device system 10B may include electrodes 24, 26, 28 and 30, along with a helix fixation member 32, which may act as or be electrically coupled to electrode 26. Lead 16C may be anchored to the wall of the coronary sinus 36, near ostium 34 via helix fixation member 32. Lead 16C may be anchored by turning the lead 16C clockwise to embed the helix fixation member 32 into the wall of the coronary sinus 36 when the electrodes are situated as desired within the heart 20. As illustrated in FIG. 4, the electrodes of lead 16 are spaced so that electrode 24 is positioned with the coronary sinus 36 distally and in close proximity to the coronary sinus ostium 34, electrode 26 is located within the coronary sinus 36 distally from and in close proximity to electrode 24, electrode 28 is located in the great cardiac vein, near the left atrium, and electrode 30 is located at the distal end of lead 16, within one of the tributary veins of the great coronary vein. For example, electrode 30 may be located in the lateral coronary vein, the anterior coronary vein, or the anterior-lateral coronary vein. The tributary vein is selected so that electrode 30 is roughly adjacent the left ventricle (LV) and not as near the right ventricle (RV) apex.

As described above, electrodes 24 and 26 may act as a bipolar pair to sense atrial activity. Electrodes 24 and 26 may be located less than approximately 1 cm apart. In some examples, electrodes 24 and 26 may be less than approximately 0.5 cm apart. The close spacing of atrial electrodes 24 and 26 may help to avoid R-wave over sensing, including far-field R-wave oversensing. In addition, the location of electrodes may aide in detecting the occurrence of an A-V block. In some examples, either of electrodes 24 and 26 may used in a unipolar configuration with an electrode formed on or by housing 14 to sense atrial activity.

In some examples, electrode 26 may serve as an atrial pace cathode, with the housing 14 of IMD 12 functioning as the atrial pace anode. Electrode 28 may serve as the ventricular sense-anode while electrode 30 may serves as the ventricular sense-cathode, or either of electrodes 28 and 30 may be used in a unipolar configurations to sense electrical activity of the ventricles. Furthermore, electrodes 28 and 30 may be used to deliver bipolar pacing or other stimulation to LV 40, or either or both of electrodes 28 and 30 may be used in a unipolar configuration with an electrode of housing 14 to deliver unipolar stimulation. The housing 14 may function as an anode when electrodes 28 or 30 stimulate. In some examples, both of electrodes 28 and 30 may be used in a unipolar configuration to deliver sequential pacing to the ventricles. For example, electrode 28 may provide a first pacing pulse. A delay of approximately 10 milliseconds may be programmed between the pacing pulse from electrode 28 and a second pacing pulse from electrode 30. During delay electrode 30 is in sensing mode. If electrode 30 senses that the pulse from electrode 28 was successful in capturing the heart, then the pacing pulse from electrode 30 is inhibited. However, if the pacing pulse from electrode 28 does not result in capture, then electrode 30 provides the second pacing pulse.

Figure 5:
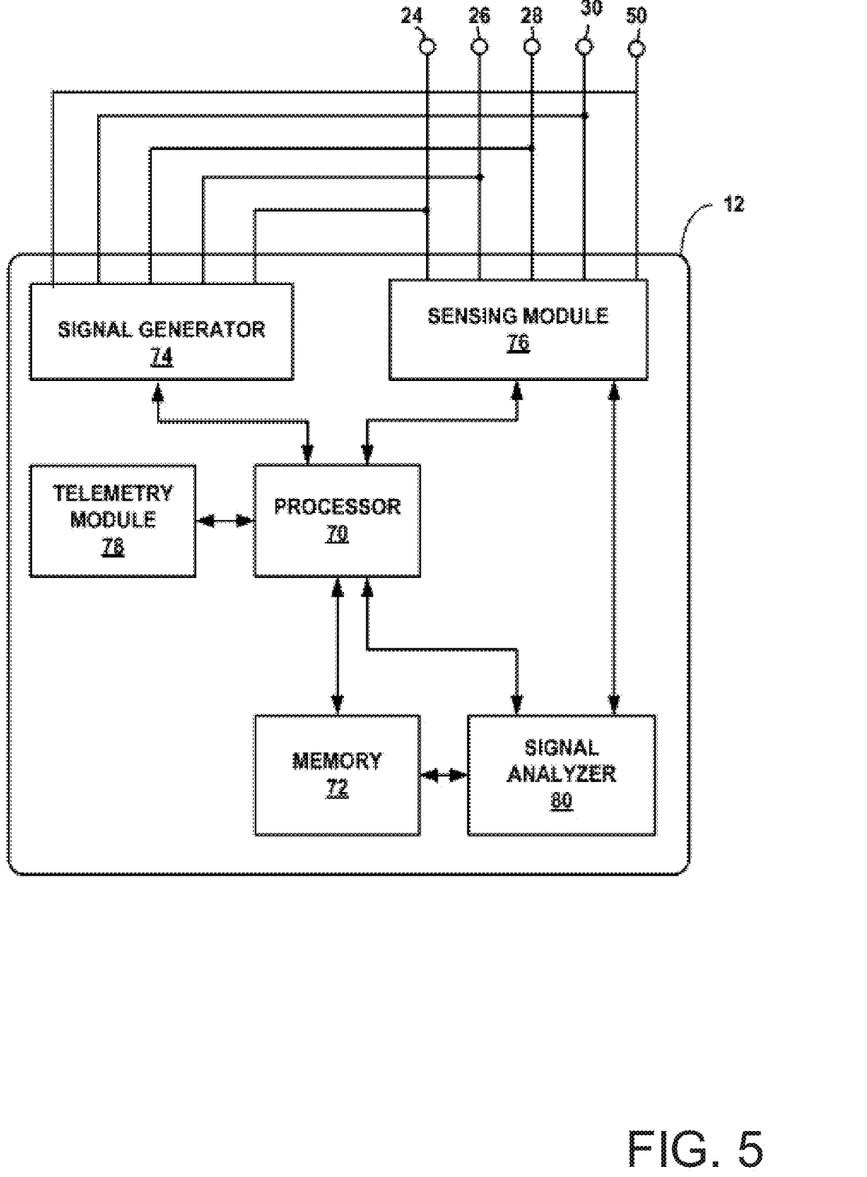
FIG. 5 is a functional block diagram of an implantable medical device system for delivering a pacing therapy, in accordance with the present disclosure.

FIG. 5 is a functional block diagram of an implantable medical device system for delivering a pacing therapy, in accordance with the present disclosure. As illustrated in FIG. 5, according to an example of the present disclosure, the IMD 12 may include a processor 70, memory 72, signal generator 74, sensing module 76, telemetry module 78, and signal analyzer 80. Memory 72 may include computer-readable instructions that, when executed by processor 70, cause IMD 12 and processor 70 to perform various functions attributed to IMD 12 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 and sensing module 76 to sense cardiac activity and deliver stimulation therapy to heart 20 of patient 18 according to a selected one or more operational modes, programs or parameters, which may be stored in memory 72.

Signal generator 74 is configured to generate and deliver electrical stimulation therapy to patient 18. As illustrated in FIG. 5, signal generator 74 is electrically coupled to electrodes 24, 26, 28 and 30 of lead 16. Signal generator 74 is also connected to a housing electrode 50 on or integral with housing 14. For example, signal generator 74 may deliver pacing pulses, to heart 20 via at least two of electrodes 24, 26, 28, 30 and 50. In other examples, signal generator 74 delivers stimulation in the form of signals other than pulses such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 24, 26, 28, 30 and 50. Sensing module 76 may also include a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense the cardiac signals. Some detection channels may detect events, such as R-waves or P-waves, and provide indications of the occurrences of such events to processor 70 and/or signal analyzer 80. One or more other detection channels may provide the signals to an analog-to-digital converter, for conversion into a digital signal for processing or analysis by processor 70 or signal analyzer 80.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76, processor 70, or signal analyzer 80. Processor 70 may analyze the digitized version of signals from the wide band channel. Processor 70 may employ digital signal analysis techniques to characterize the digitized signals from the wide band channel to, for example, detect and classify the patient's heart rhythms. In other examples, the signal analyzer 80 employs digital signal analysis techniques to characterize the digitized signals from the wide band channel.

Processor 70 may detect and classify the patient's heart rhythm based on the cardiac electrical signals sensed by sensing module 76 employing any of the numerous signal processing methodologies known in the art. In other examples, sensing module 76 provides the cardiac electrical signals sensed directed to signal analyzer 80. In some examples, sensing module 76 provides the sensed cardiac electrical signals to both processor 70 and signal analyzer 80 for different signal processing. In various examples, processor 70 may maintain escape interval counters that may reset upon sensing of R-waves by sensing modules 76. The value of the count present in the escape interval counters when reset by sensed depolarizations may be used by processor 70 to measure the durations of R-R intervals, which are measurement that may be stored in memory 72 and may be used by cardiac signal analyzer 80. Processor 70 may use the count in the interval counters to detect a tachyarrhythmia, such as ventricular fibrillation or ventricular tachycardia. A portion of memory 72 may be configured as a plurality of recirculating buffers, capable of holding a series of measured intervals, which may be analyzed by processor 70 to determine whether the patient's heart 20 is presently exhibiting atrial or ventricular tachyarrhythmia.

The duration of a cardiac cycle of a heart, which includes a depolarization-repolarization sequence, may change depending on various physiological factors of patient, such as a heart rate. As the heart rate of the patient changes, the timing of the delivery of a pacing pulse to the left ventricle during fusion pacing therapy or the timing of the delivery of pacing pulses to right ventricle and the left ventricle during biventricular pacing therapy may change. Accordingly, when an implantable medical device is delivering fusion pacing to heart, it may be useful for the device to periodically adjust a fusion pacing interval in order to maintain the delivery of the left ventricular pacing pulse at a time that results in there being fusion of the depolarization of the left and right ventricle. In addition, when the device is delivering biventricular pacing therapy to the heart, it may be useful for the device to periodically evaluate a biventricular pacing interval in order to maintain the delivery of the left ventricular pacing pulse at a time relative to the right ventricular pacing pulse that results in a synchrony of contraction of the left and right ventricle.

For example, as part of a capture management test performed by the processor 70, the device may periodically adjust the AV delay utilized during delivery of left ventricular pacing therapy by suspending or delaying delivery of the pacing therapy, and waiting a programmed length of time, such as 300 ms for example, to allow the heart of the patient to conduct in the absence of delivery of cardiac resynchronization therapy and determine whether an intrinsic, non-paced right ventricular event is sensed within the right ventricle. If an intrinsic event is determined, the device adjusts the AV delay subsequently utilized during delivery of ventricular pacing therapy by setting the pacing AV delay identified within the programmed time period.

However, since the medical device system according to the present disclosure includes only the single pass, left-sided DDD lead configuration as described above, and therefore does not include sensing electrodes positioned directly within the RV chamber via an RV lead, the device determines whether an intrinsic, non-paced event occurs by sensing intrinsic electrical cardiac activity via one or more far-field sensing vectors formed by the electrodes of the lead. The device determines far-field signal features in response to far-field cardiac signals sensed from the far-field sensing vectors for which an intrinsic, non-paced event is determined to occur, and determines a first offset interval and a second offset interval in response to the determined far-field cardiac signal features. The device then adjusts an AV delay of the LV cardiac pacing therapy in response to the determined first offset interval and second offset interval, as described below in detail.

Figure 6:
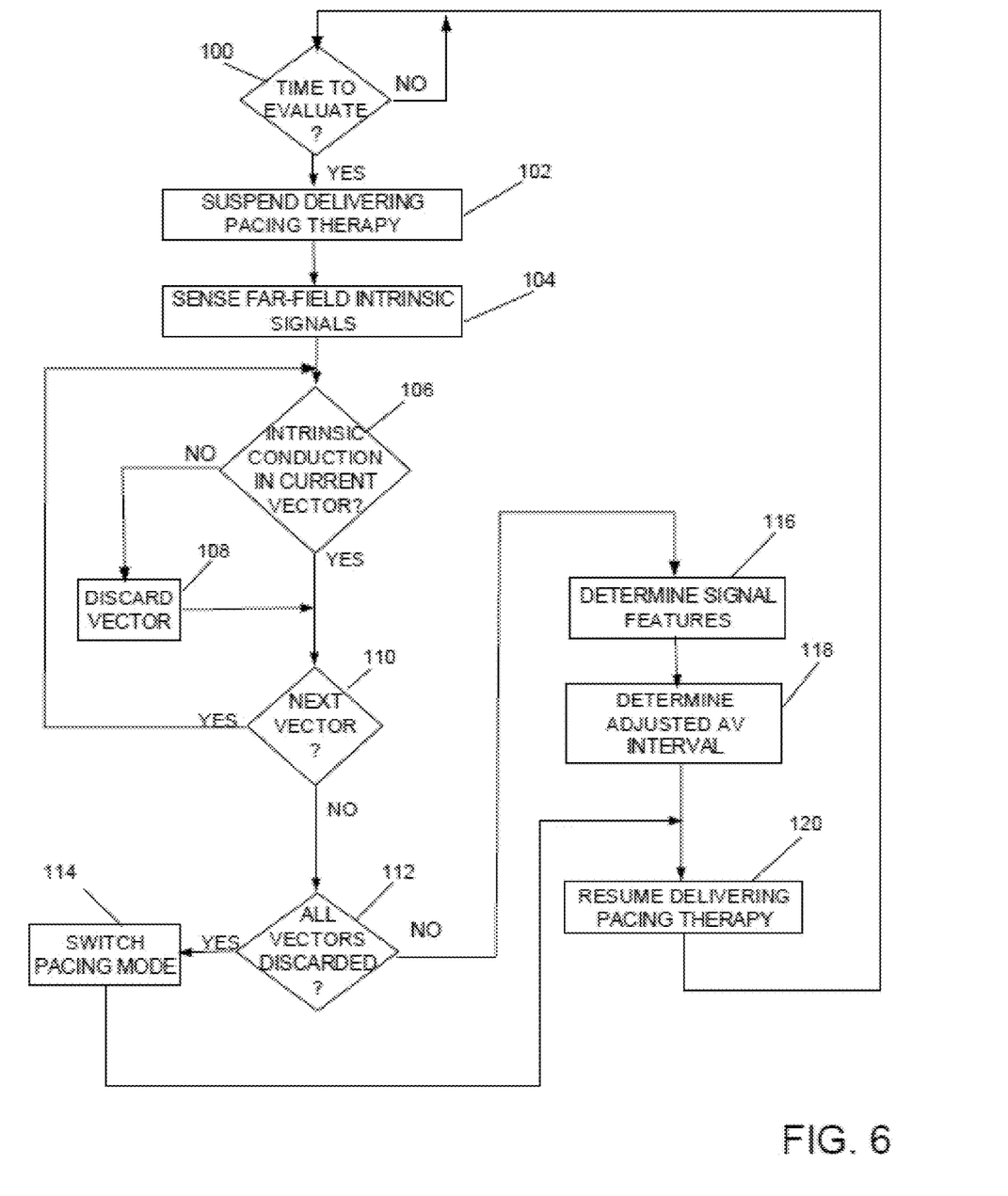
FIG. 6 is a flowchart of a method of delivering a pacing therapy in a medical device system in accordance with the present disclosure.

FIG. 6 is a flowchart of a method of delivering a pacing therapy in a medical device system in accordance with the present disclosure. According to a method of delivering a cardiac resynchronization therapy in a medical device system according to an example of the present disclosure, in order to adaptively adjust a pacing parameter, such as the AV delay for example, the processor 70 may periodically, i.e., every 60 seconds or every 120 seconds for example, suspend or delay delivery of CRT pacing therapy in order to evaluate intrinsic electrical conduction and adjust one or more pacing parameters accordingly. For example, as illustrated in FIG. 6, during the delivery of CRT LV pacing, once the processor 70 determines that it is time to evaluate intrinsic electrical conduction, Yes in Block 100, the processor 70 suspends or delays delivery of LV pacing therapy, Block 102, and senses far-field intrinsic cardiac signals, Block 104, via one or more far-field vectors. The one or more far-field vectors may include vectors formed between any combination of electrodes 24-30 of lead 16, and/or vectors formed between any number of the one or more of electrodes 24-30 of the lead 16 and the housing 14 of the device 12. For example, the device 12 may sense far-field intrinsic cardiac signals, Block 104, via a far-field sensing vector formed between electrode 24 and the electrode formed by the housing 14 of the device 12, between electrode 30 and the electrode formed by the housing 14 of the device 12, and between electrode 24 and electrode 30 of the lead 16.

During sensing of the far-field intrinsic cardiac signals, Block 104, the processor 70 determines, for each far-field vector, whether intrinsic conduction is sensed for the intrinsic cardiac signal associated with each far-field sensing vector, Block 106. For example, the processor 70 process an intrinsic signal sensed via each far-field sensing vector and determines whether an amplitude of the signal for the sensing vector exceeds an R-wave amplitude threshold within a predetermined period of time, such as 300 ms for example. If the amplitude of the signal exceeds the R-wave amplitude threshold within the predetermined period of time, an intrinsic conduction or R-wave is determined to occur, and therefore intrinsic conduction is sensed for that vector, Yes in Block 106. On the other hand, if the amplitude of the signal does not exceed the R-wave amplitude threshold within the predetermined period of time, intrinsic conduction is not sensed for that vector, No in Block 106.

In this way, a determination is made for each far-field sensing vector, i.e., the far-field sensing vector formed between electrode 24 and the electrode formed by the housing 14 of the device 12, between electrode 30 and the electrode formed by the housing 14 of the device 12, and between electrode 24 and electrode 30 of the lead 16, that either a ventricular activation attributable to intrinsic conduction of the heart is not determined to occur, No in Block 106, and therefore the far-field sensing vector is discarded, Block 108, or a ventricular activation that is attributable to intrinsic conduction of the heart is determined to occur, Yes in Block 106. Once the determination has been completed for each far-field sensing vector, No in Block 110, the processor 70 determines whether all of the far-field sensing vectors have been discarded, Block 112. If each of the far-field sensing vectors have been discarded, Yes in Block 112, the processor 70 determines that intrinsic conduction is not present and therefore causes the device to switch pacing modes, Block 114. For example, the processor 70 may cause the device to switch to an asynchronous pacing mode, such as a VVI mode.

On the other hand, if all of the far-field sensing vectors have not been discarded, No in Block 114, the processor 70 determines signal features of the intrinsic signal sensed for each of the far-field sensing vectors that were not discarded, Block 116, i.e., for the far-field vectors for which a ventricular activation that is attributable to intrinsic conduction of the heart was determined to occur, Yes in Block 106. The processor 70 then adjusts the AV interval, Block 118 based on the determined signal features, Block 116, and causes the device 12 to resume delivering the LV pacing therapy, Block 120, using the adjusted AV interval.

Figure 7:
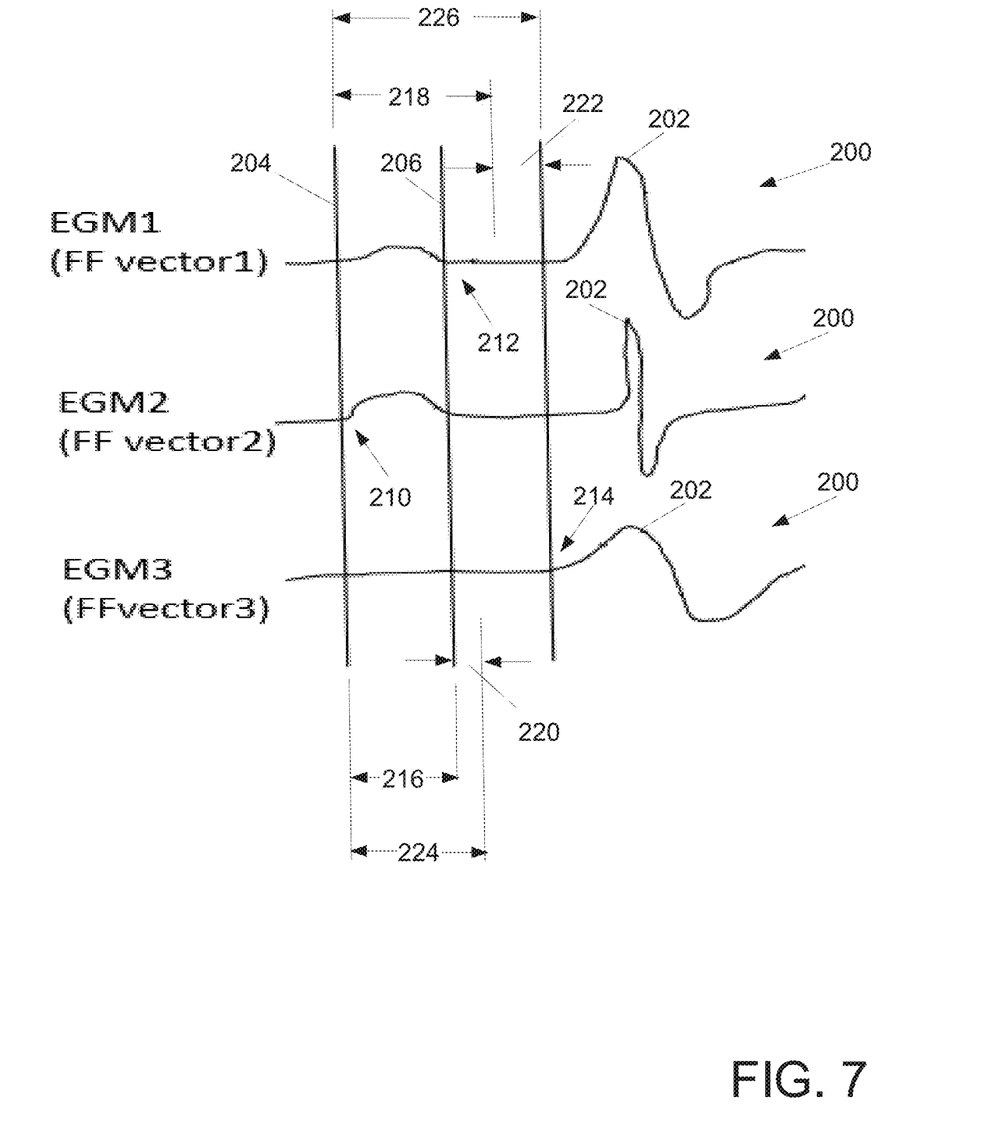
FIG. 7 is a graphical representation of sensing of a far-field intrinsic cardiac signal for adjusting delivery of a pacing therapy in a medical device system in accordance with the present disclosure.

FIG. 7 is a graphical representation of sensing of a far-field intrinsic cardiac signal for adjusting delivery of a pacing therapy in a medical device system in accordance with the present disclosure. As illustrated in FIG. 7, during the determination of signal features for each far-field sensing vector for which intrinsic conduction is determined to occur, Block 116 of FIG. 6, the processor 70 senses a far-field cardiac signal 200 in each far-field sensing vector. In the example of FIG. 7, far-field (FF) sensing vectors formed between electrode 24 and the electrode formed by the housing 14 of the device 12, FF vector1, between electrode 30 and the electrode formed by the housing 14 of the device 12, FF vector2, and between electrode 24 and electrode 30 of the lead 16, FF vector3 are utilized. Intrinsic conduction is determined to occur for each of the far-field vectors since each of the corresponding cardiac signals 200 are determined to have an amplitude 202 that exceeds the amplitude threshold within the predetermined period of time, Yes in Block 106 of FIG. 6.

Figure 8:
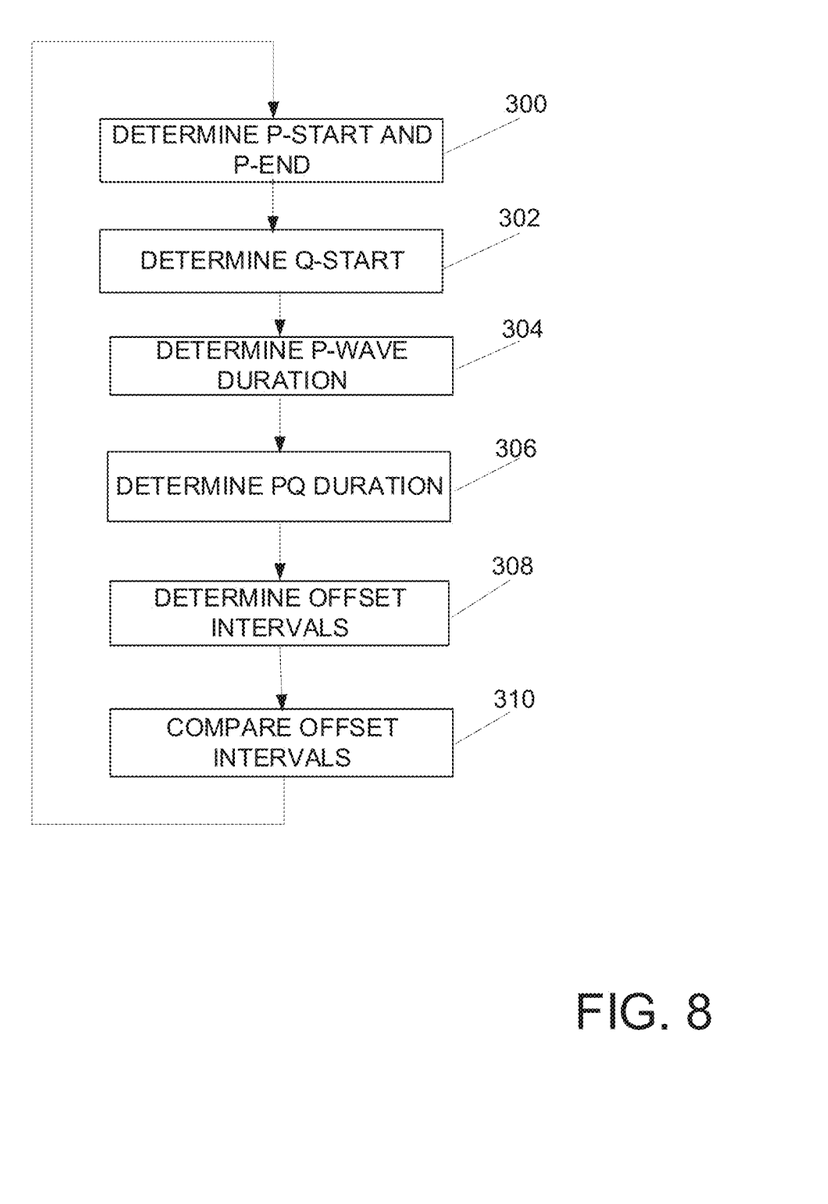
FIG. 8 is a flowchart of determining far-field signal features for adjusting an LV pacing therapy in accordance with the present disclosure.

FIG. 8 is a flowchart of determining far-field signal features for adjusting an LV pacing therapy in accordance with the present disclosure. As illustrated in FIGS. 7 and 8, during the determining of far-field signal features, Block 120 of FIG. 6, the processor 70 processes each far-field cardiac signal 200 and determines a start of a P-wave 205 and an end of a P-wave 206, Block 300, along with a start of a QRS complex 208, based on the sensed far-field signals 200, Block 302. In one example, the processor 70 may determine the start of the P-wave may 204 as being the earliest deflection 210 of the cardiac signals 200 sensed by three far-field vectors, which in the example of FIG. 7 occurs in the cardiac signal 200 of the second far-field sensing vector, FF vector2. In the same way, the processor 70 may determine the end of the P-wave 206 as being the latest deflection 212 of the cardiac signals 200 sensed by three far-field vectors that occurs immediately after the first or earliest deflection 210. In the example of FIG. 7 the latest deflection 212 occurs in the cardiac signal 200 of the first far-field sensing vector, FF vector1. Similarly, the processor 70 may determine the start of the QRS complex 208 as being the earliest deflection 214 of the cardiac signals 200 sensed by three far-field vectors that occurs immediately after or subsequent to the latest deflection 212, which in the example of FIG. 7 occurs in the cardiac signal 200 of the third far-field sensing vector, FF vector3.

Other methods may be utilized to determine the start of the P-wave 204, the end of the P-wave 206, and the start of the QRS complex 208. For example, the processor 70 may determine an average of the first deflections that occur for each of the cardiac signals 200 sensed by the three far-field sensing vectors in which a P-wave is determined to occur (no P-wave occurs in the far-field signal 200 of the third far-field sensing vector FF vector3) to determine the start of the P-wave 204, and the average of the subsequent deflections of the cardiac signals 200 sensed by three far-field vectors immediately after the first deflections. The processor then similarly determines the average of the third deflections of the far-field cardiac signals 200 sensed by the three far-field vectors that occur immediately after the subsequent deflections previously determined to occur immediately after the first deflections.

In addition to determining the start of the P-wave 204, the end of the P-wave 206, Block 300, and the start of the QRS complex 208, Block 302, the processor 70 determines a P-wave duration 216, Block 304, extending from the start of the P-wave 204 to the end of the P-wave 206, and a PQ duration 226 extending from the start of the P-wave 204 to the start of the QRS complex 208, Block 306. Once the P-wave duration 216 and the PQ duration 226 have been determined, the processor 70 determines offset intervals, Block 308, by adding a first offset 220 to the P-wave duration 216 to generate a first offset interval 224 and subtracting a second offset 222 from the PQ duration 226 to generate a second offset interval 218. The offsets 220, 222 are programmable, and in one example, the first offset 220 may be set as 30 ms and the second offset 222 may be set as 50 ms.

The processor 70 then compares the first offset interval 224 and the second offset interval 218, Block 310, and determines the adjusted AV interval, Block 122 of FIG. 6 based on the comparison. For example, the processor 70 may adjust the AV interval to be the earliest of the first offset interval 224 and the second offset interval 218, which in the example of FIG. 7 is the first offset interval 224. To illustrate, assuming that the first offset is set as 30 ms and the second offset 222 is set as 50 ms, if the PQ duration 226 is determined to be 190 ms and the P-wave duration 216 is determined to be 100 ms, the second offset interval 218, i.e., PQ duration 228—second offset 222, would be determined to be 140 ms and the first offset interval 224, i.e., P-wave duration 216+first offset 220, would be determined to be 130 ms. Therefore, since the first offset interval 224 is less than the second offset interval 218 and therefore the earliest, the processor 70 adjusts the AV interval to be equal to the first offset interval 224. As a result, the processor 70 causes the device 12 to resume delivering the LV pacing therapy, Block 120 of FIG. 6, with the adjusted AV interval set to the value of the earliest of the first offset interval 224 and the second offset interval 218.

Figure 9:
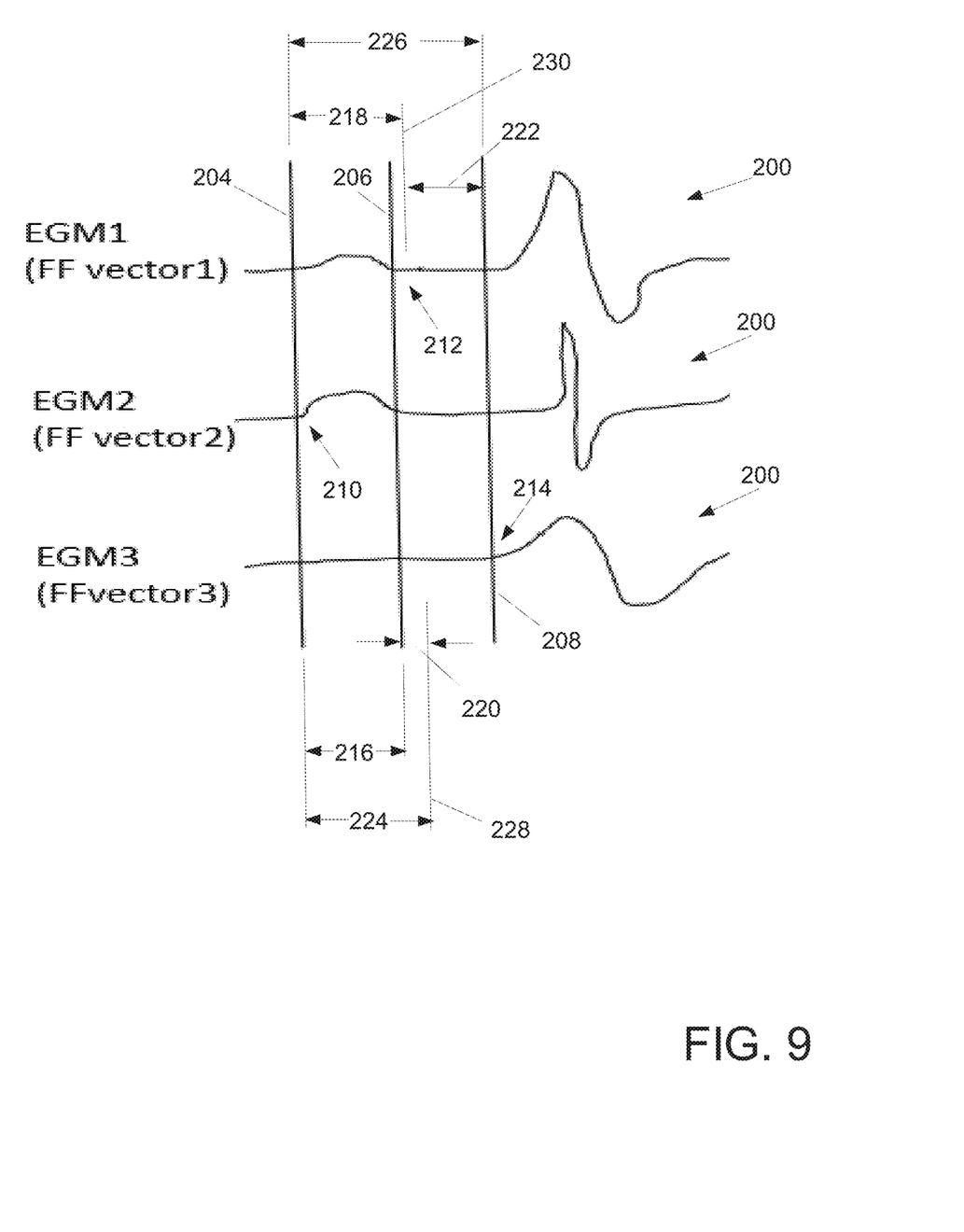
FIG. 9 is a graphical representation of sensing of a far-field intrinsic cardiac signal for adjusting delivery of a pacing therapy in a medical device system in accordance with the present disclosure.

FIG. 9 is a graphical representation of sensing of a far-field intrinsic cardiac signal for adjusting delivery of a pacing therapy in a medical device system in accordance with the present disclosure. In the example illustrated in FIG. 9, the earliest of the first offset interval 224 and the second offset interval 218 is the second offset interval 218. As a result, the processor 70 causes the device 12 to resume delivering the LV pacing therapy, Block 120 of FIG. 6, with the adjusted AV interval set to the value of the second offset interval 218.

The techniques described in this disclosure, including those attributed to the IMD 12, processor 70, the programmer 22, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A method for delivering a left ventricular (LV) cardiac pacing therapy to a patient, comprising:
   suspending delivery of the LV cardiac pacing therapy;
   sensing far-field cardiac signals via one or more far-field sensing vectors formed between a plurality of electrodes;
   determining far-field signal features of the sensed far-field cardiac signals;
   determining a first offset interval and a second offset interval using the determined far-field signal features;
   adjusting an AV delay of the LV cardiac pacing therapy using the determined first and second offset intervals; and
   resuming delivery of the LV cardiac pacing therapy having the adjusted AV delay.

2. The method of claim 1, wherein the plurality of electrodes are positioned on a single-pass coronary sinus lead.

3. The method of claim 1, wherein determining far-field signal features of the sensed far-field cardiac signals comprises:

determining a start of a P-wave, an end of the P-wave, and a start of a QRS complex of the sensed far-field cardiac signals;

determining a P-wave duration extending from the start of the P-wave to the end of the P-wave and a PQ duration extending from the start of the P-wave to the start of the QRS complex;

determining the first offset interval using the P-wave duration; and determining the second offset interval using the PQ duration.

4. The method of claim 3, wherein determining far-field signal features of the sensed far-field cardiac signals comprises:

determining a first deflection along each of the far-field cardiac signals sensed by each of the one or more far-field sensing vectors to generate first occurring deflections;

determining the start of the P-wave as being the earliest of the first occurring deflections;

determining a second deflection along each of the far-field cardiac signals sensed by each of the one or more far-field vectors that occurs immediately after the first deflection to generate second occurring deflections;

determining the end of the P-wave as being the earliest of the second occurring deflections;

determining a third deflection along each of the far-field cardiac signals sensed by each of the one or more far-field sensing vectors that occurs immediately after the second deflection to generate third occurring deflections; and determining the start of the QRS complex as being the earliest of the third occurring deflections.

5. The method of claim 3, wherein determining the first offset interval comprises determining a sum of the P-wave duration and a first offset.

6. The method of claim 5, wherein determining the second offset interval comprises reducing the PQ duration by a second offset.

7. The method of claim 6, wherein the first offset is set as 30 milliseconds and the second offset is set as 50 ms.

8. The method of claim 1, further comprising determining the earliest of the first offset interval and the second offset interval, wherein adjusting the AV delay comprises setting the AV delay equal to the determined earliest of the first offset interval and the second offset interval.

9. The method of claim 1, further comprising:

determining, for each of the far-field cardiac signals sensed by each of the one or more far-field sensing vectors, whether intrinsic conduction is being sensed; and determining the far-field signal features for only the far-field sensing vectors for which intrinsic conduction is being sensed.

10. The method of claim 1, wherein determining far-field signal features of the sensed far-field cardiac signals comprises:

determining a first deflection along each of the far-field cardiac signals sensed by each of the one or more far-field sensing vectors to generate first occurring deflections;

determining a start of a P-wave as being the earliest of the first occurring deflections;

determining a second deflection along each of the far-field cardiac signals sensed by each of the one or more far-field vectors that occurs immediately after the first deflection to generate second occurring deflections;

determining an end of the P-wave as being the earliest of the second occurring deflections;

determining a third deflection along each of the far-field cardiac signals sensed by each of the one or more far-field sensing vectors that occurs immediately after the second deflection to generate third occurring deflections; and determining a start of a QRS complex as being the earliest of the third occurring deflections;

determining a P-wave duration extending from the start of the P-wave to the end of the P-wave and a PQ duration extending from the start of the P-wave to the start of the QRS complex;

wherein the first offset interval comprises a sum of the P-wave duration and a first offset to generate the first offset interval and the second offset interval comprises the PQ duration reduced by a second offset; and wherein adjusting an AV delay of the LV cardiac pacing therapy using the determined first and second offset intervals comprises:

determining the earliest of the first offset interval and the second offset interval, and setting the AV delay equal to the determined earliest of the first offset interval and the second offset interval.

11. An implantable medical device system for delivering a cardiac pacing therapy to a patient, comprising:

an implantable medical device housing;

a single-pass coronary sinus lead capable of being electrically coupled to the housing;

a plurality of electrodes positioned along the single-pass coronary sinus lead to sense a far-field cardiac signal of the patient and to deliver cardiac pacing therapy; and a processor positioned within the housing and configured to suspend delivery of the LV cardiac pacing therapy, sense far-field cardiac signals via one or more far-field sensing vectors formed between a plurality of electrodes, determine far-field signal features of the sensed far-field cardiac signals, determine a first offset interval and a second offset interval using the determined far-field signal features, adjust an AV delay of the LV cardiac pacing therapy using the determined first and second offset intervals, and resume resuming delivery of the LV cardiac pacing therapy having the adjusted AV delay.

12. The medical device system of claim 11, wherein, to determine far-field signal features of the sensed far-field cardiac signals, the processor is further configured to determine a start of a P-wave, an end of the P-wave, and a start of a QRS complex of the sensed far-field cardiac signals, determine a P-wave duration extending from the start of the P-wave to the end of the P-wave and a PQ duration extending from the start of the P-wave to the start of the QRS complex, determine the first offset interval using the P-wave duration, and determine the second offset interval using the PQ duration.

13. The medical device system of claim 12, wherein, to determine far-field signal features of the sensed far-field cardiac signals, the processor is further configured to determine a first deflection along each of the far-field cardiac signals sensed by each of the one or more far-field sensing vectors to generate first occurring deflections, determine the start of the P-wave as being the earliest of the first occurring deflections, determine a second deflection along each of the far-field cardiac signals sensed by each of the one or more far-field vectors that occurs immediately after the first deflection to generate second occurring deflections, determine the end of the P-wave as being the earliest of the second occurring deflections, determine a third deflection along each of the far-field cardiac signals sensed by each of the one or more far-field sensing vectors that occurs immediately after the second deflection to generate third occurring deflections, and determine the start of the QRS complex as being the earliest of the third occurring deflections.

14. The medical device system of claim 12, wherein the first offset interval comprises a sum of the P-wave duration and a first offset.

15. The medical device system of claim 14, wherein the second offset interval comprises the PQ duration reduced by a second offset.

16. The medical device system of claim 15, wherein the first offset is set as 30 milliseconds and the second offset is set as 50 ms.

17. The medical device system of claim 11, wherein the processor is configured to determine the earliest of the first offset interval and the second offset interval, wherein adjusting the AV delay comprises setting the AV delay equal to the determined earliest of the first offset interval and the second offset interval.

18. The medical device system of claim 11, wherein the processor is configured to determine, for each of the far-field cardiac signals sensed by each of the one or more far-field sensing vectors, whether intrinsic conduction is being sensed, and determine the far-field signal features for only the far-field sensing vectors for which intrinsic conduction is being sensed.

19. The medical device system of claim 11, wherein, to determine far-field signal features of the sensed far-field cardiac signals, the processor is further configured to determine a first deflection along each of the far-field cardiac signals sensed by each of the one or more far-field sensing vectors to generate first occurring deflections, determine a start of a P-wave as being the earliest of the first occurring deflections, determine a second deflection along each of the far-field cardiac signals sensed by each of the one or more far-field vectors that occurs immediately after the first deflection to generate second occurring deflections, determine an end of the P-wave as being the earliest of the second occurring deflections, determine a third deflection along each of the far-field cardiac signals sensed by each of the one or more far-field sensing vectors that occurs immediately after the second deflection to generate third occurring deflections, determine a start of a QRS complex as being the earliest of the third occurring deflections, wherein the first offset interval comprises a sum of the P-wave duration and a first offset and the second offset interval comprises the PQ duration reduced by a second offset, and wherein the processor is further configured to determine the earliest of the first offset interval and the second offset interval, wherein adjusting the AV delay comprises setting the AV delay equal to the determined earliest of the first offset interval and the second offset interval.

20. A non-transitory computer readable medium storing instructions which cause an implantable medical device to perform a method, the method comprising:
 suspending delivery of a left ventricular (LV) cardiac pacing therapy;
 sensing far-field cardiac signals via one or more far-field sensing vectors formed between a plurality of electrodes positioned on a single-pass coronary sinus lead;
 determining far-field signal features of the sensed far-field cardiac signals;
 determining a first offset interval and a second offset interval using the determined far-field signal features;
 adjusting an AV delay of the LV cardiac pacing therapy using the determined first offset interval and second offset interval; and
 resuming delivery of the LV cardiac pacing therapy having the adjusted AV delay.

* * * * *